(12) United States Patent
Carter et al.

(10) Patent No.: US 8,075,877 B2
(45) Date of Patent: Dec. 13, 2011

(54) BROAD SPECTRUM IMMUNE AND ANTIVIRAL GENE MODULATION BY ORAL INTERFERON

(75) Inventors: William A. Carter, Spring City, PA (US); David R Strayer, Bryn Mawr, PA (US)

(73) Assignee: Hemispherx Biopharma, Philadelphia, PA (US)

( * ) Notice: Subject to any disclaimer, the term of this patent is extended or adjusted under 35 U.S.C. 154(b) by 465 days.

(21) Appl. No.: 11/713,097

(22) Filed: Mar. 2, 2007

(65) Prior Publication Data

US 2009/0004141 A1    Jan. 1, 2009

Related U.S. Application Data

(60) Provisional application No. 60/780,079, filed on Mar. 8, 2006.

(51) Int. Cl.
*A61K 38/21* (2006.01)
*A61K 38/00* (2006.01)

(52) U.S. Cl. ......... 424/85.4; 424/85.7; 514/1.5; 514/3.7

(58) Field of Classification Search ......................... None
See application file for complete search history.

(56) References Cited

U.S. PATENT DOCUMENTS

| | | | |
|---|---|---|---|
| 4,950,652 A | 8/1990 | Carter | |
| 5,019,382 A * | 5/1991 | Cummins, Jr. ............... | 424/85.4 |
| 5,910,304 A | 6/1999 | Cummins | |
| 6,372,218 B1 | 4/2002 | Cummins | |
| 6,509,154 B1 | 1/2003 | de Paillette | |
| 7,339,051 B2 | 3/2008 | Crooke et al. | |
| 2005/0002901 A1 | 1/2005 | Blatt | |
| 2005/0100885 A1 | 5/2005 | Crooke et al. | |
| 2005/0137154 A1 | 6/2005 | Carter et al. | |
| 2006/0024271 A1 | 2/2006 | Alibek et al. | |
| 2006/0035859 A1 | 2/2006 | Carter et al. | |
| 2007/0141080 A1 | 6/2007 | Carter et al. | |
| 2008/0019943 A1 | 1/2008 | Carter et al. | |
| 2009/0004141 A1 | 1/2009 | Carter et al. | |

FOREIGN PATENT DOCUMENTS

| | | |
|---|---|---|
| WO | 2004/013298 | 2/2004 |
| WO | 2004/092383 | 10/2004 |
| WO | 2005/009337 | 2/2005 |
| WO | 2005/019410 | 3/2005 |
| WO | 2006/082435 | 8/2006 |

OTHER PUBLICATIONS

Kuiken et al, "Pathology of Human Influenza A (H5N1) . . . ", Vet Pathol 40:304-310 (2003).
deJong et al, "Fatal Outcome of Human Influenza A (H5N1) . . . ", Nature Medicine, Advance Online Publication; 2006.
Barnard et al. "Evaluation of immunomodulators, interferons and known in vitro SARS-coV inhibitors for inhibition of SARS-coV replication in BALB/c" Antiviral Chem. Chemother. 17:275-284 (2006).
Business Wire "Arnpligen® enhances the effectiveness of Tamiflu against avian influenza: Second independent preclinical study confirms dsRNA increases flu vaccine effectiveness" two pages (Sep. 2005).
Business Wire "Hemispherx Biopharma expands evaluation of Alferon N against avian flu, promising effects in bird populations to be expanded based on WHO/UN findings" two pages (Feb. 2005).
D'Agostini et al. "Combination therapy with amantadine and immunomodulators potentiates antiviral effects in influenza A virus-infected mice" Antiviral Res. 20(suppl 1):160 (abstract 217) (Apr. 1993).
Dahl et al. "In vitro inhibition of SARS virus replication by human interferons" Scand. J. Infect. Dis. 36:829-831 (Dec. 2004).
Hayden et al. "Combined interferon-$\alpha_2$, rimantadine hydrochloride, and ribavirin inhibition of influenza virus replication in vitro" Antimicrobiol. Agents Chemother. 25:53-57 (Jan. 1984).
Houston Chronicle "Anti-virus drug relieves chronic fatigue syndrome" p. 20 (Oct. 1991).
Ison & Hayden "Therapeutic options for the management of influenza" Curr. Opin. Pharm. 1:482-490 (Oct. 2001).
Pharma Business Week "Avian influenza, Ampligen enhances the effectiveness of Tamiflu against avian influenza" p. 18 (Oct. 2005).
Subbarao & Roberts "Is there an ideal animal model for SARS?" Trends Microbiol. 14:299-303 (Jul. 2006).
Tan et al. "Inhibition of SARS coronavirus infection in vitro with clinically approved antiviral drugs" Emerging Infect. Dis. 10:581-586 (Apr. 2004).
World Health Organization "Management of severe acute respiratory syndrome (SARS)" two pages (Nov. 2003).
Zhao et al. "Description and clinical treatment of an early outbreak of severe acute respiratory syndrome (SARS) in Guangzhou, PR China" J. Med. Microbiol. 52:715-720 (Aug. 2003).
Int'l Search Report and Preliminary Report on Patentability for PCT/US2007/005634 (Jun. 2008).
Extended search report (EESR) for related European Patent Application, Serial No. 07867004.9, mailed Sep. 14, 2009.
Office Action issued in connection with U.S. Appl. No. 11/812,361 mailed Jul. 23, 2009.
Shen, F., et al., "The immunomodulation and antiviral activity of human leucocyte interferon alpha orally administered in mice", Chinese Journal of Biochemical Pharmaceutics, 2004, vol. 25, No. 3, pp. 141-143, including Abstract, published Dec. 31, 2004.

* cited by examiner

*Primary Examiner* — Christine J Saoud
*Assistant Examiner* — Jegatheesan Seharaseyon
(74) *Attorney, Agent, or Firm* — Nixon & Vanderhye, P.C.

(57) ABSTRACT

An antiviral/immunomodulatory response in an animal is induced by oral administration to an infected animal, including humans, of a human α-interferon. Methods of conferring resistance or mitigating the effects of exposure to a virus including avian influenza are described.

17 Claims, No Drawings

BROAD SPECTRUM IMMUNE AND ANTIVIRAL GENE MODULATION BY ORAL INTERFERON

CROSS REFERENCE TO RELATED APPLICATION

This application claims priority from U.S. provisional patent application Ser. No. 60/780,079 filed Mar. 8, 2006.

The present invention relates to the use of α-interferon composed of a mixture of naturally occurring α-interferons, and optionally other components for activating an immune response for combating the effects of viral infections such as avian influenza (AVI).

Viral infection of human cells results in activation of an innate immune response (the first line of defense) mediated by type 1 interferons, notably interferon-alpha (α). This normally leads to activation of an immunological "cascade", as interferon-α, acting as a type of conductor of the immune "orchestra", synchronizes the timing and relative amounts of various mediators (also termed cytokines or lymphokines) which compose the immune orchestra. If the immune orchestra conductor, specifically interferon-α, is inactivated, the orchestra members thereafter play erratically, out of sequence, etc., and the cumulative effect, rather than being beneficial and pleasant, may actually be very detrimental to the human body. Lethal acute human viruses may typically inactivate interferon-α in order to get a "foothole" within the human body Prototypic viruses behaving in this manner are avian influenza virus, SARS virus, smallpox virus, and others that may kill the human host in a matter of hours, or several days (similar effects are seen in veterinary populations).

Recent examination of the lung pathology (at post mortem) indicated that, with destruction/incapacitation of the immune orchestra conductor, interferon-α, certain mediator/"players" overreact causing immune-mediated damage to the lungs, potentially leading to death. Animal-based studies and human data (reported herein as the subject invention) indicate that the immune-inappropriate and potentially lethal, immune dysregulation, can be reregulated appropriately by small doses of interferon-α applied briefly to the oral/buccal mucosa, either before or during early stages of otherwise overwhelming infections.

Examination of lung pathology in avian influenza not only reveals tissue injury, but also oxidative damage, pulmonary edema and hemorrhage. Interferon-α [ALFERON N used herein, a "cocktail" of 8 different molecular species of interferon from a human family of approximately 20 alpha interferons] can reverse these changes by inducing antiviral/immunomodulatory genes upon brief oral exposure. We document herein up to 385 such relevant genes which are temporarily induced by ALFERON N to perform a coordinated attack against lethal viruses.

Geiss et al. (Proc Natl Acad-Sci, Aug. 6, 2002, vol 99, no 16) reported that lung epithelial pathology in pandemic influenza was due to "blocking the expression of interferon-regulated genes". Others have pointed to "profound activation of the inflammatory response", much of this being due to inappropriate expression of TNF (tumor necrosis factor), an immunoregulatory lymphokine which is effectively down-regulated by practicing the present invention.

Conspicuously, the subject invention reactivates the relevant interferon immunomodulatory pathways without significant upregulation of the inflammatory cytokines—TNF being the best studied prototypic example.

The α-interferon component of the therapeutic procedures herein described is preferably based upon ALFERON N INJECTION® the only approved natural, multi-species, α-interferon available in the United States. It is the first natural source, multi-species interferon and is a consistent mixture of at least seven species of α-interferon. In contrast, the other available α-interferons are single molecular species of α-interferon made in bacteria using DNA recombinant technology. These single molecular species of α-interferon also lack an important structural carbohydrate component because this glycosylation step is not performed during the bacterial process.

Unlike species of α-interferon produced by recombinant techniques, ALFERON N INJECTION® is produced by human white blood cells which are able to glycosylate the multiple α-interferon species. Reverse Phase HPLC studies show that ALFERON N INJECTION® is a consistent mixture of at least seven species of alpha interferon ($\alpha 2$, $\alpha 4$, $\alpha 7$, $\alpha 8$, $\alpha 10$, $\alpha 16$, $\alpha 17$). This natural-source interferon has unique anti-viral properties distinguishing it from genetically engineered interferons. The high purity of ALFERON N INJECTION® and its advantage as a natural mixture of seven interferon species, some of which, like species 8b, have greater antiviral activities than other species, for example, species 2b, which is the only component of Intron A. The superior antiviral activities for example in the treatment of chronic hepatitis C virus (HCV) and HIV and tolerability of ALFERON N INJECTION® compared to other available recombinant interferons, such as Intron A and Roferon A, have been reported.

ALFERON N INJECTION® is available as an injectable solution containing 5,000,000 International Units (IU) per ml.

For internal administration the α-interferon may, for example, be formulated in conventional manner for oral, nasal or buccal administration. Formulations for oral administration include aqueous solutions, syrups, elixirs, powders, granules, tablets and capsules which typically contain conventional excipients such as binding agents, fillers, lubricants, disintegrants, wetting agents, suspending agents, emulsifying agents, preservatives, buffer salts, flavoring, coloring and/or sweetening agents.

α-interferon may be administered for therapy preferably by a suitable route including oral, nasal or topical (including transdermal, buccal and sublingual). It will be appreciated that the preferred route will vary with the condition and age of the recipient, the nature of the infection and the chosen active ingredient.

The recommended dosage of the components will depend on the clinical status of the patient and the experience of the clinician in treating similar infection. As a general guideline, dosage of ALFERON N INJECTION® utilized for systemic infections is 5 to 10 million units (sq) thrice weekly. Experience to date is with dosages above 3 IU/lb of patient body weight. Oral α-interferon (ALFERON LDO) has been administered as a liquid solution in the range of 500-2000 IU/day and calculated on the basis of a 150 pound human this is 3.3 to 13.3 IU/lb per day.

Our experience indicates beneficial results are obtained at dosage levels of α-interferon in excess of 450 IU, that is greater than 3 IU/pound body weight. These amounts are in contrast to and greater than Cummins use in U.S. Pat. No. 5,910,304 of alpha interferon administration to the pharyngeal mucosa orally or as lozenge or tablet.

Exposure of the oromucosa to low doses of alpha interferon has been reported to lead to biological effects in animals and humans. However, the optimal dose/schedule of low dose oral α-interferon to achieve a systemic antiviral effect is determined by the clinician. A naturally derived alpha α-interferon (ALFERON N INJECTION®) has been approved for treatment of *condylomata acuminata*. It is active at doses significantly lower than those used for recombinant alpha α-interferon.

EXAMPLE 1

This study was conducted to determine the prophylactic efficacy of ALFERON against Influenza H5N1 infection in cynomolgus macaques.

Cynomolgus macaques (*Macaca fascicularis*) were infected with Influenza virus H5N1, demonstrated that the clinical signs in the macaques resemble those found in humans infected with the Avian Influenza H5N1 viruses, thus allowing the infection of cynomolgus macaques with Influenza H5N1 viruses to serve as a model for these infections in humans (Rimmelzwaan et al. Avian Dis. 2003; 47(3 Suppl): 931-3, Kuiken et al. Vet Pathol. 2003 May; 40(3):304-10, Rimmelzwaan et al. J. Virol. 2001 July; 75(14):6687-91).

The macaque H5N1 infection model described above was used to determine the prophylactic efficacy of ALFERON in the cynomolgus macaque following oro-mucosal delivery of ALFERON to cynomolgus macaque following oro-mucosal delivery of ALFERON to cynomolgus macaques starting five days before intratracheal challenge with Influenza virus A/Vietnam/1194/'04 (H5N1), and followed by daily dosing for ten days at various doses.

Animals were anaesthetized before each procedure for safety and practical reasons (oro-mucosal delivery of ALFERON and infection with Influenza virus H5N1). The experiment consisted of four groups of three animals each. Group A was treated with 10 mg/kg ALFERON, group B with 25 mg/kg ALFERON group C with 62.5 mg/kg ALFERON and group D with placebo. There were no adverse effects observed.

Upon euthanasia at day 5 after infection macroscopic lung lesions indicated that animals from group C treated with 62.5 mg/kg ALFERON showed no separated dark red area(s) or diffuse dark areas on the lungs in contrast to animals of the other groups. This is consistent with the microscopic findings which indicate also a lower grade of primary atypical pneumonia in both left cranial- and caudal lung lobes in animals of this group.

Prophylactic treatment of macaques with oro-mucosal delivery of ALFERON appears to have a beneficial dose dependent effect with reduced gross- and histo pathology in treated animals.

EXAMPLE 2

Study A: asymptomatic HIV infected subjects with CD4 levels>400 were treated with 500 IU or 1,000 IU of ALFERON® in an aqueous buffered solution prepared by diluting ALFERON® for injection administered orally daily for 10 days. RNA from peripheral blood leukocytes was isolated from blood collected before, during and post-therapy using Paxgene technology for RNA isolation. A cDNA microarray analysis was utilized to identify genes which were modulated as a result of the ALFERON® oral dosing. Study B: normal healthy volunteers being studied in a similar manner.

Initial results in Study A indicate an induction of α-interferon related gene activity in peripheral blood leukocytes following the oral administration of 500 IU or 1,000 IU of a multi-species natural leukocyte α-interferon.

ALFERON® used in the study was supplied as a liquid solution packaged in sealed polypropylene lined foil pouches. Each pouch contained 1.0 ml of ALFERON® (500 IU or 1,000 IU) or placebo. Solutions were taken orally each day for 10 days. No food or water is taken 30 minutes prior to through 30 minutes after administration. Dosing and blood sampling are shown in Table 1. Dose effects are in Tables 2-4.

TABLE 1

| Study Day Number and Event | | | | | | | | | | | | | | | | | |
|---|---|---|---|---|---|---|---|---|---|---|---|---|---|---|---|---|---|
| | Day Number | | | | | | | | | | | | | | | | |
| | 0* | 1 | 2 | 3 | 4 | 5 | 6 | 7 | 8 | 9 | 10 | 11 | 12 | 13 | 14 | 15 | 16 |
| LDO Dosing | | X | X | X | X | X | X | X | X | X | X | | | | | | |
| Blood Samples Drawn | ↑ B1 + B2 | | ↑ T1 | | | ↑ T2 | | | | | | ↑ T3 | ↑ T4 | | | | ↑ T5 |

*Day 0 = Baseline period in which two separate samples (B1 and B2) are drawn.
Goal: Compare gene expression of T1-T5 Samples to two Baseline Samples Combined (i.e. B1 + B2)

Blood samples were subjected to a cDNA Microarray Analysis as follows:

Array construction. The array used in this study comprised a subset of sequence verified cDNA clones from the Research Genetics Inc. 40,000 clone set representing 950 genes containing adenylate/uridylate rich elements and 18 genes potentially involved in AU-directed mRNA decay, 855 ISGs representing an expansion of a previously described clone set containing confirmed and candidate genes stimulated by IFNs in diverse cell types, 288 genes responsive to the viral analog poly(I).poly(C), and 85 housekeeping genes.

Target RNA preparation. Target RNA was generated in a T7 polymerase based linear amplification reaction. Two μg total RNA and 5 pmol of t7-(dT)24 primer (5'GGCCAGTGAATTGTAATACGACTCACTATAGGGAGGCGG-(dT) 24-3' (SEQ ID NO: 1) in a total volume of 5.5 μl was incubated at 70° C. for 10 min and chilled on ice. For first strand cDNA synthesis, the annealed RNA template was incubated for 1 h at 42° C. in a 10 μl reaction containing first strand buffer (Invitrogen), 10 mM DTT, 1 U per μl anti-RNase (Ambion), 500 μM dNTPs and 2 U per μl Superscript II, (Invitrogen). Second strand was for 2 h at 16° C. in a total reaction volume of 50 μl containing first strand reaction products, second strand buffer (Invitrogen), 250 μM dNTPs, 0.06 U per μl DNA ligase (Ambion), 0.26 Upper μl DNA polymerase I, (NEB) and 0.012 U per μl RNase H (Ambion) followed by the addition of 3.3 U of T4 DNA polymerase (3 U per μl; New England Biolabs) and a further 15 min incubation at 16° C. Second strand reaction products were purified by phenol:chloroform:isoamyl alcohol extraction in Phaselock microcentrifuge tubes (Eppendorf) according to manufacturer's instructions and ethanol precipitated. In vitro transcription was performed using the T7 megascript kit (Ambion) according to a modified protocol in which purified cDNA was combined with 1 µl each 10×ATP, GTP, CTP and UTP and 1 µl T7 enzyme mix in a 10 µl reaction volume and incubated for 9 h at 37° C. Amplified RNA was purified using the Rneasy RNA purification kit (Ambion).

RNA labeling. Cy3 or Cy5 labeled cDNA was prepared by indirect incorporation. Two µg of amplified RNA, 1 µl dT12-18 primer (1 µg per µl, Invitrogen), 2.6 µl random hexanucleotides (3 µg per µl, Invitrogen) and 1 µl anti-RNAse (Ambion) were combined in a reaction volume of 15.5 µl and incubated for 10 min at 70° C. Reverse transcription was for 2 h at 42° C. in a 30 µl reaction containing annealed RNA template, first strand buffer, 500 mM each dATP, dCTP, dGTP, 300 µM dTTP, 200 µM aminoallyl-dUTP (Sigma), 10 mM DTT, 12.7 U per µl Superscript II. For template hydrolysis, 10 µl of 0.1M NaOH was added to the reverse transcription reaction and the mixture was incubated for 10 min at 70° C., allowed to cool at room temperature for 5 min and neutralized by addition of 10 µl 0.1M HCl. cDNA was precipitated at −20° C. for 30 min after addition of 1 µl linear acrylamide (Ambion), 4 µl 3M NaAc (pH 5.2) and 100 µl absolute ethanol then resuspended in 5 µl of 0.1M NaHCO3. For dye-coupling the contents of 1 tube of NHS ester containing Cy3 or Cy5 dye (Amersham Biosciences) was dissolved in 45 µl DMSO. Five µl dye solution was mixed with the cDNA and incubated for 1 h in darkness at room temperature. Labeled cDNA was purified on a QIAQUICK PCR purification column (Qiagen) according to manufacturer's instructions. Eluted cDNA was dried under vacuum and resuspended in 30 µl of Slidehyb II hybridization buffer (Ambion). After 2 min denaturation at 95° C. the hybridization mixture was applied to the microarray slide under a coverslip. Hybridization proceeded overnight in a sealed moist chamber in a 55° C. waterbath. Post-hybridization, slides were washed successively for 5 min each in 2×SSC 0.1% SDS at 55° C., then 2×SSC at 55° C. plus a final 5 min wash in 0.2×SSC at room temperature.

Data acquisition and normalization. Data were acquired with a GenePix 4000B laser scanner and GenePix Pro 5.0 software. Raw data were imported into GeneSpring 6.0 software (Silicon Genetics) and normalized based on the distribution of all values with locally weighted linear regression (LOESS) before further analysis.

Initial results in Study A indicate that orally administered ALFERON® was well tolerated at the 500 and 1,000 IU/day dosage levels. cDNA microarray analysis identified 385 genes that were expressed >two fold over baseline in two or more patient samples. As shown in Tables 2, 3 and 4 an approximately four fold increase in gene expression was seen at the 1,000 IU/day dosage level compared to 500 IU/day (p<0.0001). Although, not an exhaustive list, Table 5 shows 25 genes that were expressed >two fold over baseline in ≧33% of patient samples. PDZ and LIN domain 5 and 2'-5' oligoadenylate synthetase-like were among the top five upregulated genes. 2'-5' oligoadenylate synthetase is an important component of the interferon intracellular antiviral pathway. Importantly, as shown in Table 6, genes related to activation of an inflammatory response such as tumor necrosis factor (TNF) related genes were down regulated.

Recent evidence shows that the virulence of influenza A including avian (H5N1) isolates correlates with the ability of the non-structural NS1 viral protein to bind to human PDZ domains and thereby abrogating the expression of antiviral genes in host cells including interferon pathways (Science xpress, 26 Jan. 2006). Thus, the finding that orally administered ALFERON®) can upregulate PDZ domain expression raises the possibility that ALFERON® could have an important role in abrogating the ability of influenza viruses including avian (H5N1) to evade human host defense mechanisms.

The orally administered ALFERON® was well-tolerated with no serious adverse events reported. Only several mild adverse events were reported, such as a metallic taste in mouth or flatulence/bloating. There were no clinically significant changes in laboratory parameters and no changes in Karnofsky Performance Status (KPS).

Experiments to date indicate that a biological cocktail of natural human interferon species administered orally has systemic biological activity based on upregulation of α-interferon related genes in peripheral blood leukocytes. Because alpha α-interferon are broad spectrum antiviral/immunomodulatory molecules, potential applications in numerous α-interferon-sensitive diseases exist, including application to respiratory infections such as avian influenza.

TABLE 2

Number of Genes with Expression Increased ≧2 Fold Over Baseline in Two or More Patient Samples

| Dose | 500 IU | | | | 1,000 IU | | | | Fold Increase |
|---|---|---|---|---|---|---|---|---|---|
| Patient # | 1 | 2 | 3 | Mean | 4 | 5 | 6 | Mean | of Mean |
| Day 2 | 10 | 1 | 39 | 16.7 | 85 | 77 | 108 | 90 | 5.4 |
| Day 5 | 14 | 4 | 23 | 13.7 | 54 | 72 | 35 | 54 | 3.9 |
| Day 11 | 1 | 8 | 4 | 4.3 | 4 | 45 | 40 | 30 | 6.9 |
| Day 12 | 3 | 15 | — | 9.0 | 19 | 44 | 28 | 30 | 3.4 |
| Day 16 | — | 14 | — | 14 | 3 | 59 | 48 | 37 | 2.6 |
| Mean | 7.0 | 8.4 | 22 | 12.5 | 33 | 59 | 52 | 48 | 3.9 |

Student's t-test, p-value < 0.0001 (n = 385)

TABLE 3

Dose Effect: Number of Genes with Expression Increased ≧2 Fold Over Baseline in Three or More Patient Samples

| Dose | 500 IU | | | | 1,000 IU | | | | Fold Increase |
|---|---|---|---|---|---|---|---|---|---|
| Patient # | 1 | 2 | 3 | Mean | 4 | 5 | 6 | Mean | of Mean |
| Day 2 | 3 | 1 | 19 | 7.6 | 36 | 41 | 42 | 39.7 | 5.2 |
| Day 5 | 2 | 2 | 6 | 3.3 | 16 | 17 | 16 | 16.3 | 4.9 |
| Day 11 | 1 | 1 | 1 | 1.0 | 3 | 3 | 3 | 3.0 | 3.0 |
| Day 12 | 1 | 2 | — | 1.5 | 7 | 8 | 8 | 7.7 | 5.1 |
| Day 16 | — | 0 | — | 0 | 2 | 2 | 2 | 2.0 | >5 |
| Mean | 1.8 | 1.2 | 8.7 | 3.9 | 12.8 | 14.2 | 14.2 | 13.7 | 3.5 |

Student's t-test, p-value < 0.0001 (n = 252)

TABLE 4

Dose Effect: Number of Genes with Expression Increased ≧3 Fold Over Baseline in Two or More Patient Samples

| Dose | 500 IU | | | | 1,000 IU | | | | Fold Increase |
|---|---|---|---|---|---|---|---|---|---|
| Patient # | 1 | 2 | 3 | Mean | 4 | 5 | 6 | Mean | of Mean |
| Day 2 | 0 | 0 | 9 | 3.0 | 23 | 10 | 37 | 23.0 | 7.8 |
| Day 5 | 5 | 1 | 5 | 3.7 | 16 | 19 | 4 | 13.0 | 3.5 |
| Day 11 | 1 | 2 | 0 | 1.0 | 0 | 14 | 3 | 5.7 | 5.7 |
| Day 12 | 1 | 3 | — | 2.0 | 3 | 10 | 2 | 5.0 | 2.5 |
| Day 16 | — | 0 | — | 0.0 | 0 | 14 | 6 | 6.7 | >5 |
| Mean | 1.8 | 1.2 | 4.7 | 2.6 | 8.4 | 13.4 | 10.4 | 10.7 | 4.1 |

Student's t-test, p-value < 0.0001 (n = 69)

TABLE 5

Genes Expressed ≧ Two Fold Over Baseline in ≧ 33% of Patient Samples

| Identified Gene | Expression Frequency (%) | | |
|---|---|---|---|
| | 500 IU | 1,000 IU | Overall |
| 1 SFRS protein kinase 1 | 83 | 40 | 59 |
| 2 *Homo sapiens*, clone image: 5164031, mRNA | 17 | 87 | 56 |
| 3 PDZ and LIN domain 5 | 0 | 93 | 52 |
| 4 Interleukin 17 receptor | 0 | 93 | 52 |
| 5 2'-5' oligoadenylate synthetase-like | 33 | 67 | 52 |
| 6 Similar to KIAA0160 gene product | 0 | 87 | 48 |
| 7 N-myristoyltransferase 2 | 0 | 80 | 44 |
| 8 Proteasome (prosome, macropain) 26S subunit, ATPase, 6 | 0 | 73 | 41 |
| 9 Coagulation factor II (thrombin) receptor | 0 | 73 | 41 |
| 10 Cytochrome P450, family 51, subfamily A, polypeptide | 0 | 73 | 41 |
| 11 Interferon induced transmembrane protein 2 | 33 | 47 | 41 |
| 12 Major histocompatibility complex, class I, F | 33 | 47 | 41 |
| 13 Sarcoglycan, beta (43 kDa dystrophin-associated glycoprotein) | 0 | 73 | 41 |
| 14 Glutamate dehydrogenase 1 | 0 | 73 | 41 |
| 15 FGG | 0 | 67 | 37 |
| 16 Coagulation factor III (thromboplastin, tissue factor) | 0 | 67 | 37 |
| 17 Interferon (alpha, beta, and omega) receptor 1 | 0 | 67 | 37 |
| 18 Ribosomal protein S6 kinase, 90 KDa, polypeptide 3 | 0 | 60 | 33 |
| 19 Hemoglobin, epsilon 1 | 33 | 33 | 33 |
| 20 Acyl-coenzyme A dehydrogenase, short/branched chain | 0 | 60 | 33 |
| 21 Hypothetical protein MGC20481 | 17 | 47 | 33 |
| 22 RAB7, member RAS oncogene family | 17 | 47 | 33 |
| 23 Ribosomal protein S15a | 0 | 60 | 33 |
| 24 Glutamate dehydrogenase I | 0 | 60 | 33 |
| 25 Small nuclear RNA activating complex, polypeptide 3, 50 KDa | 25 | 40 | 33 |

TABLE 6

Five Tumor Necrosis Factor (TNF) Related Genes with a 50% or Greater Reduction in Expression 1. TNF (ligand) superfamily, member 11
2. TNF receptor superfamily, member 6b, decoy
3. TNF receptor - associated factor 1
4. TNF, alpha-induced protein 6
5. TNF receptor superfamily, member 10b

We claim:

1. A method of inducing an antiviral/immunomodulatory response in an animal comprising orally or nasally administering to an infected animal α-interferon in an amount of at least 6.6 IU per round of the animal's body weight so that the antiviral/immunomodulatory response is induced.

2. The method of claim 1 wherein the α-interferon was purified as a mixture of at least seven species of α-interferon produced by human white blood cells.

3. The method of claim 2 wherein the α-interferon species are orally administered to a human in an amount in the range of 1000-2000 IU per day.

4. The method of claim 2 wherein the α-interferon species are orally administered to a human in an amount of at least 6.6 IU per pound of the human's body weight.

5. The method of claim 2 wherein the α-interferon species are orally administered to a human in an amount in the range of 1000-2000 IU per day.

6. The method of claim 2 wherein the α-interferon species are nasally administered to a human in an amount in the range of 1000-2000 IU per day.

7. The method of claim 2 wherein the α-interferon species are nasally administered to a human in an amount of at least 6.6 IU per pound of the human's body weight.

8. The method of claim 7 wherein the α-interferon species are nasally administered to a human in an amount in the range of 1000-2000 IU per day.

9. A method of systemically activating an innate immune response comprising orally or nasally administering to an animal α-interferon in an amount of at least 6.6 µl per pound of the animal's body weight so that the innate immune response is activated.

10. The method of claim 9 wherein the α-interferon was purified as a mixture of at least seven species of α-interferon produced by human white blood cells.

11. The method of claim 10 wherein the α-interferon species are orally administered to a human in an amount of at least 6.6 IU per pound of the human's body weight.

12. The method of claim 11 wherein the α-interferon species are orally administered to a human in an amount in the range of 1000-2000 IU per day.

13. The method of claim 10 wherein the α-interferon species are orally administered to a human in an amount in the range of 1000-2000 IU per day.

SEQUENCE LISTING

<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ggccagtgaa ttgtaatacg actcactata gggaggcggt tttttttttt tttttttttt    60
ttt                                                                  63

14. The method of claim 10 wherein the α-interferon species are nasally administered to a human in an amount of at least 6.6 IU per pound of the human's body weight.

15. The method of claim 14 wherein the α-interferon species are nasally administered to a human in an amount in the range of 1000-2000 IU per day.

16. The method of claim 10 wherein the α-interferon species are nasally administered to a human in an amount in the range of 1000-2000 IU per day.

17. The method of claim 1 or 9 wherein the animal is a human.

* * * * *